US009993001B2

(12) United States Patent
Yamada et al.

(10) Patent No.: US 9,993,001 B2
(45) Date of Patent: Jun. 12, 2018

(54) HERBICIDAL COMPOSITION

(71) Applicant: ISHIHARA SANGYO KAISHA, LTD., Osaka (JP)

(72) Inventors: Ryu Yamada, Osaka (JP); Hiroyuki Okamoto, Osaka (JP); Yoshifumi Saito, Osaka (JP); Takashi Terada, Osaka (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days. days.

(21) Appl. No.: 15/520,929

(22) PCT Filed: Oct. 14, 2015

(86) PCT No.: PCT/JP2015/079069
§ 371 (c)(1),
(2) Date: Apr. 21, 2017

(87) PCT Pub. No.: WO2016/063778
PCT Pub. Date: Apr. 28, 2016

(65) Prior Publication Data
US 2017/0332642 A1 Nov. 23, 2017

(30) Foreign Application Priority Data
Oct. 22, 2014 (JP) ................. 2014-215428

(51) Int. Cl.
| *A01N 47/30* | (2006.01) |
| --- | --- |
| *A01N 37/34* | (2006.01) |
| *A01N 33/18* | (2006.01) |
| *A01N 37/22* | (2006.01) |
| *A01N 43/70* | (2006.01) |
| *A01N 47/12* | (2006.01) |

(52) U.S. Cl.
CPC ............. *A01N 47/30* (2013.01); *A01N 33/18* (2013.01); *A01N 37/22* (2013.01); *A01N 37/34* (2013.01); *A01N 43/70* (2013.01); *A01N 47/12* (2013.01)

(58) Field of Classification Search
None
See application file for complete search history.

(56) References Cited

U.S. PATENT DOCUMENTS

| 2008/0153704 A1 | 6/2008 | Yamaji et al. |
| 2011/0028325 A1 | 2/2011 | Sievernich et al. |
| 2012/0058896 A1 | 3/2012 | Yamaji et al. |
| 2013/0085065 A1 | 4/2013 | Kikugawa et al. |
| 2014/0106971 A1 | 4/2014 | Kikugawa et al. |
| 2014/0228217 A1 | 8/2014 | Yamada et al. |

FOREIGN PATENT DOCUMENTS

| CA | 1247880 A | 1/1989 |
| EP | 0163598 A1 | 12/1985 |
| GB | 1473105 A | 5/1977 |
| JP | 50-069230 A | 6/1975 |
| JP | 60-233003 A | 11/1985 |
| JP | 2013-28589 A | 2/2013 |
| JP | 2013-216601 A | 10/2013 |
| WO | 2008/075743 A1 | 6/2008 |
| WO | 2009/115420 A2 | 9/2009 |
| WO | 2011/158843 A1 | 12/2011 |

OTHER PUBLICATIONS

Adigun et al., (Chemical weed control in irrigated sweet pepper(*Capsicum annuum* L.), Tropical Pest Management (1991), 37(2), 155-8).*
Mordalski et al., "Broadleaf weed and grass weed control in common borage", Progress in Plant Protection, 2003, pp. 825-828, vol. 43. (w/ English Abstract on last page).
"Patoran 500 SC", Oct. 22, 2003, PP. [online] <URL:http://www.toxpro.be/risquemetier/agriculture/FDS/PQR/Patoran%20500%20SC.pdf>. (cited in ISR submitted as cite No. 8).
Anyszka et al., "Grass Weeds Control in Snap Bean With Graminicide Fusilade Forte 150 EC (Fluazifop-P-Buthyl)", Progress in Plant Proctection, 2001, pp. 904-906, vol. 41. (w/ English Abstract on last page).
Lagoke et al., "Chemical weed control in rainfed cowpea (*Vigna unguiculata* (L.) Walp) in the Guinea savanna zone of Nigeria", Weed Research, 1982, pp. 17-22, vol. 22.
Lyubenov et al., "Effect of some combinations and systems of herbicides on quantity and quality of sunflower oil", Rastenievudni Nauki, 1992, pp. 132-136, vol. 29. (w/ English Abstract on last page).
Angelova, "Residual effect of some methods for weed control in beans on the following wheat crop", Rastenievudni Nauki, 1978, pp. 205-211, vol. 15, vol. 9-10. (w/ English Abstract on last page).
Hoffmann, "Weed control in peas", Novenyvedelem, vol. 29, Iss. 1-2, ISSN: 0133-0829, CAPlus (STN), 1993, pp. 53-67.
International Search Report (ISR) in International Patent Application No. PCT/JP2015/079069, dated Jan. 19, 2016.
IPRP in PCT/JP2015/079069, dated May 4, 2017.

* cited by examiner

Primary Examiner — Alton N Pryor
(74) Attorney, Agent, or Firm — Greenblum & Bernstein, P.L.C.

(57) ABSTRACT

To provide a highly active herbicidal composition to control undesired plants by synergistic herbicidal effects.
The present invention provides a herbicidal composition comprising (A) metobromuron or its salt, and (B) at least one herbicidal compound selected from the group consisting of chlorpropham, S-metolachlor, flufenacet, pyroxasulfone, nicosulfuron, fluazifop-P-butyl, prometryn, ioxynil, pendimethalin, trifluralin, prosulfocarb, thiobencarb and indanofan, or its alkyl ester or its salt; and a herbicidal method of using it.

20 Claims, No Drawings

HERBICIDAL COMPOSITION

TECHNICAL FIELD

The present invention relates to a herbicidal composition and a method for controlling undesired plants.

BACKGROUND ART

Patent Document 1 discloses a composition comprising a urea derivative of the formula (I) including metobromuron, and another herbicide. Patent Document 2 discloses a composition comprising pyroxasulfone and another herbicide. Patent Document 3 discloses a herbicidal composition comprising flazasulfron or its salt, and at least one herbicidal compound selected from the group consisting of tebuthiuron, diuron and metobromuron, or its salt.

However, in Patent Documents 1, 2 and 3, there is no specific disclosure or suggestion for combining (A) metobromuron and (B) at least one herbicidal compound selected from the group consisting of chlorpropham, S-metolachlor, flufenacet, pyroxasulfone, nicosulfuron, fluazifop-P-butyl, prometryn, ioxynil, pendimethalin, trifluralin, prosulfocarb, thiobencarb and indanofan, or its alkyl ester or its salt. Further, it is not known that such a combination exhibits synergistic herbicidal effects.

PRIOR ART DOCUMENTS

Patent Documents

Patent Document 1: European Patent Application Publication No. 163598
Patent Document 2: WO2009/115420
Patent Document 3: WO2011/158843

DISCLOSURE OF INVENTION

Technical Problem

Many herbicidal compositions have been developed and presently used, but they may not necessarily be sufficient to control undesired plants including weeds to be controlled. Therefore, development of a highly active herbicidal composition is desired.

It is an object of the present invention to provide a herbicidal composition which exhibits high herbicidal effects at a low dose against undesired weeds and which exhibits synergistic herbicidal effects.

Solution to Problem

The present inventors have conducted extensive studies, and they have found it possible to obtain a highly active herbicidal composition by combining specific compounds and thus have accomplished the present invention.

That is, the present invention relates to a herbicidal composition comprising (A) metobromuron or its salt (hereinafter referred to as the compound A), and (B) at least one herbicidal compound selected from the group consisting of chlorpropham, S-metolachlor, flufenacet, pyroxasulfone, nicosulfuron, fluazifop-P-butyl, prometryn, ioxynil, pendimethalin, trifluralin, prosulfocarb, thiobencarb and indanofan, or its alkyl ester or its salt (hereinafter referred to as the compound B). Further, the present invention relates to a method for controlling undesired plants or inhibiting their growth, which comprises applying a herbicidally effective amount of the compound A and a herbicidally effective amount of the compound B to the undesired plants or to a place where they grow.

Advantageous Effects of Invention

According to the present invention, it is possible to provide a herbicidal composition which exhibits highly active synergistic herbicidal effects against undesired plants and which is highly safe to crop plants, and a method for controlling undesired plants or inhibiting their growth.

When the herbicidal activity in a case where two active ingredients are combined, is larger than the simple sum of the respective herbicidal activities of the two active ingredients (the expected activity), it is called a synergistic effect. The activity expected by the combination of two active ingredients can be calculated as follows (Colby S. R., "Weed", vol. 15, p. 20-22, 1967).

$$E=\alpha+\beta-(\alpha\times\beta+100)$$

where $\alpha$: growth inhibition rate when treated with x (g/ha) of herbicide X,
  $\beta$: growth inhibition rate when treated with y (g/ha) of herbicide Y,
  E: growth inhibition rate expected when treated with x (g/ha) of herbicide X and y (g/ha) of herbicide Y.

That is, when the actual growth inhibition rate (measured value) is larger than the growth inhibition rate by the above calculation (calculated value), the activity by the combination can be regarded as showing a synergistic effect. The herbicidal composition of the present invention shows a synergistic effect when calculated by the above formula.

DESCRIPTION OF EMBODIMENTS

As the compound A, metobromuron (common name) is 3-(4-bromophenyl)-1-methoxy-1-methylurea.

Now, the compound B will be described in detail.

Chlorpropham (common name) is isopropyl 3-chlorocarbanilate.

S-metolachlor (common name) is 2-chloro-N-(6-ethyl-o-tolyl)-N-[(1S)-2-methoxy-1-methylethyl]acetamide.

Flufenacet (common name) is 4'-fluoro-N-isopropyl-2-[5-(trifluoromethyl)-1,3,4-thiadiazol-2-yloxy] acetanilide.

Pyroxasulfone (common name) is 3-[5-(difluoromethoxy)-1-methyl-3-(trifluoromethyl)pyrazol-4-yl methylsulfonyl]-4,5-dihydro-5,5-dimethyl-1,2-oxazole.

Nicosulfuron (common name) is 2-[(4,6-dimethoxypyrimidin-2-yl carbamoyl)sulfamoyl]-N,N-dimethyl nicotinamide.

Fluazifop-P-butyl (common name) is butyl (R)-2-[4-[5-(trifluoromethyl)-2-pyridyloxy]phenoxy] propionate.

Prometryn (common name) is $N^2,N^4$-diisopropyl-6-methylthio-1,3,5-triazine-2,4-diamine.

Ioxynil (common name) is 4-hydroxy-3,5-diiodobenzonitrile, and its alkyl ester may, for example, be ioxynil octanoate.

Pendimethalin (common name) is N-(1-ethylpropyl)-2,6-dinitro-3,4-xylidine.

Trifluralin (common name) is $\alpha,\alpha,\alpha$-trifluoro-2,6-dinitro-N,N-dipropyl-p-toluidine.

Prosulfocarb (common name) is S-benzyl dipropyl(thiocarbamate).

Thiobencarb (common name) is S-4-chlorobenzyl diethyl (thiocarbamate).

Indanofan (common name) is (RS)-2-[2-(3-chlorophenyl)-2,3-epoxypropyl]-2-ethyl indane-1,3-dione The compound A or the compound B may sometimes form an alkyl ester or a salt or may sometimes have an isomer, in addition to the above-mentioned ones, and such an ester, salt or isomer is included in the present invention, so long as it is agriculturally acceptable.

The mixing ratio of the compound A to the compound B cannot be generally defined, since it is required to be suitably adjusted depending upon the type of the formulation, the weather conditions, the types and growth stages of undesired plants, etc. However, it is, for example, from 200:1 to 1:40, preferably from 60:1 to 1:25, more preferably from 50:1 to 1:6, by weight ratio. Further, more detailed mixing ratios of the compound A to the compound B will be listed in Table 1.

TABLE 1

| Compound B | Mixing ratios of the compound A to the compound B (A:B) (weight ratio) | |
|---|---|---|
| | Preferred range | More preferred range |
| Chlorpropham | 8:1 to 1:8 | 3:1 to 1:6 |
| S-Metolachlor | 8:1 to 1:8 | 2:1 to 1:1 |
| Flufenacet | 20:1 to 1:8 | 7:1 to 1:1 |
| Pyroxasulfone | 100:1 to 1:1 | 50:1 to 7:1 |
| Nicosulfuron | 66.7:1 to 1:1 | 35:1 to 30:1 |
| Fluazifop-P-butyl | 20:1 to 1:4 | 6:1 to 1:1 |
| Prometryn | 20:1 to 1:12 | 5:1 to 1:1 |
| Ioxynil | 40:1 to 1:8 | — |
| Pendimethalin | 8:1 to 1:8 | 4:1 to 1:1 |
| Trifluralin | 8:1 to 1:8 | 2:1 to 1:2 |
| Prosulfocarb | 4:1 to 1:16 | 1:1 to 1:6 |
| Thiobencarb | 2:1 to 1:8 | 2:1 to 1:3 |
| Indanofan | 100:1 to 1:2 | 25:1 to 4:1 |

The herbicidally effective amounts of the compound A and the compound B cannot be generally defined, since it is required to be suitably adjusted depending upon the mixing ratio of the compound A to the compound B, the type of the formulation, the weather conditions, the types and growth stages of undesired plants, etc., but, for example, the compound A is from 100 to 4,000 g/ha, and the compound B is from 20 to 4,000 g/ha, preferably the compound A is from 60 to 1,500 g/ha, and the compound B is from 25 to 1,500 g/ha.

The herbicidal composition of the present invention may be applied to undesired plants or may be applied to a place where they grow. Further, it may be applied at any time either before or after the emergence of the undesired plants. Further, the herbicidal composition of the present invention may take various application forms such as soil application, foliar application, irrigation application, and submerged application, and it can be applied to agricultural fields such as upland fields, orchards and paddy fields, and non-cropland such as ridges of fields, fallow fields, play grounds, golf courses, vacant lands, forests, factory sites, railway sides and roadsides.

The herbicidal composition of the present invention can control a broad range of undesired plants such as annual weeds and perennial weeds. The undesired plants to be controlled by the herbicidal composition of the present invention may, for example, be cyperacrae such as green kyllinga (*Kyllinqa brevifolia* Rottb. var. *leiolepis*), or sedge (*Cyperus* spp.) [the sedge may, for example, be purple nutsedge (*Cyperus rotundus* L.), smallflower umbrella sedge (*Cyperus difformis* L.), yellow nutsedge (*Cyperus esculentus* L.) or amur *cyperus* (*Cyperus microiria* Steud.)]; gramineae such as barnyardgrass (*Echinochloa crus-galli* L., *Echinochloa oryzicola* vasing.), japanese millet (*Echinochloa utilis* Ohwi et Yabuno), crabgrass (*Digitaria* spp.) [the crabgrass may, for example, be summergrass (*Digitaria ciliaris* (Retz.) Koel), large crabgrass (*Digitaria sanquinalis* L.), violet crabgrass (*Digitaria violascens* Link) or *Digitaria horizontalis* Wind], green foxtail (*Setaria viridis* L.), giant foxtail (*Setaria faberi* Herrm.), goosegrass (*Eleusine indica* L.), johnsongrass (*Sorghum halepense* (L.) Pers.), bermudagrass (*Cynodon dactylon* (L.) Pers.), wild oat (*Avena fatua* L.), annual bluegrass (*Pao annua* L.), panic grass (*Panicum* spp.) [the panic grass may, for example, be guinea grass (*Panicum maximum* Jacq.), or fall *panicum* (*Panicum dichotomiflorum* (L.) Michx.)], signal grass (*Brachiaria* spp.) [the signal grass may, for example, be plantain signal grass (*Brachiaria plantaginea* (LINK) Hitchc.), palisade signal grass (*Brachiaria decumbens* Stapf), or mauritius signal grass (*Brachiaria mutica* (Forssk.) Stapf)], *paspalum* (*Paspalum* spp.), itchgrass (*Rottboellia cochinchinensis* (LOUR.) W. D. CLAYTON), southern sandbur (*Cenchrus echinatus* L.), or shattercane (*Sorghum bicolor* (L) Moench.), italian ryegrass (*Lolium multiflorum* Lam.); scrophulariaceae such as persian speedwell (*Veronica persica* Poir.), or corn speedwell (*Veronica arvensis* L.); compositae such as beggar ticks (*Bidens* spp.) [the beggar ticks may, for example, be hairy beggarticks (*Bidens pilosa* L.), devils berggarticks (*Bidens frondosa* L.), *Bidens biternata* (Lour.) Merr. et Sherif), or beggarticks (*Bidens subalternans* DC.)], hairy fleabane (*Conyza bonariensis* (L.) Cronq.), horseweed (*Eriqeron canadensis* L.), dandelion (*Taraxacum officinale* Weber), or common cocklebur (*Xanthium strumarium* L.); lequminosae such as rattlepod or rattlebox (*Crotalaria* spp.) [the rattlepod or rattlebox may, for example, be sunn-hemp (*Crotalaria juncea* L.)], poison bean (*Sesbania* spp.) [the poison bean may, for example, be rostrate sesbania (*Sesbania rostrata* Bremek. & Oberm.) or sesbania pea (*Sesbania cannabina* (Retz.) Pers.)], white clover (*Trifolium repens* L.); caryophyllaceae such as sticky chickweed (*Cerastium qlomeratum* Thuill.), or common chickweed (*Stellaria media* L.); euphorbiaceae such as garden spurge (*Euphorbia hirta* L.), threeseeded copperleaf (*Acalypha australis* L.), or fireplant (*Euphorbia heterophylla* L.); plantaginaceae such as asiatic plantain (*Plantago asiatica* L.); oxalidaceae such as creeping woodsorrel (*Oxalis corniculata* L.); apiaceae such as lawn pennywort (*Hydrocotyle sibthorpioides* Lam.); violaceae such as violet (*Viola mandshurica* W. Becker); iridaceae such as blue-eyedgrass (*Sisyrinchium rosulatum* Bicknell): qeraniaceae such as caroling geranium (*Geranium carolinianum* L.); labiatae such as purple deadnettle (*Lamium purpureum* L.). or henbit (*Lamium amplexicaule* L.); malvaceae such as velvetleaf (*Abutilon theophrasti* MEDIC.), or prickly sida (*Sida spinosa* L.); convolvulaceae such as ivy-leaved morningglory (*Ipomoea hederacea* (L.) Jacq.), common morningglory (*Ipomoea purpurea* ROTH), cypressvine morningglory (*Ipomoea quamoclit* L.), *Ipomoea qrandifolia* (DAMMERMANN) O'DONNELL, hairy merremia (*Merremia aeqyptia* (L.) URBAN), or field Bindweed (*Convolvulus arvensis* L.); chenopodiaceae such as common lambsquarters (*Chenopodium album* L.); portulacaceae such as common purslane (*Portulaca oleracea* L.); amaranthaceae such as pigweed (*Amaranthus* spp.) [the pigweed may, for example, be prostrate pigweed (*Amaranthus blitoides* S. Wats:), livid amaranth (*Amaranthus lividus* L.), purple amaranth (*Amaranthus blitum* L.), smooth pigweed (*Amaranthus hybridus* L.), *Amaranthus patulus* Bertol., powell amaranth (*Amaranthus powellii* S. Wats.), slender amaranth (*Amaranthus viridis* L.), palmer amaranth (*Amaranthus palmeri* S. Wats.), redroot pigweed (*Amaranthus retroflexus* L.), tall waterhemp (*Amaranthus tuberculatus*

(Moq.) Sauer.), common waterhemp (*Amaranthus tamariscinus* Nutt.), thorny amaranth (*Amaranthus spinosus* L.), ataco (*Amaranthus quitensis* Kunth.), or *Amaranthus rudis* Sauer]: solanaceae such as black nightshade (*Solanum nigrum* L.); polygonaceeae such as spotted knotweed (*Polygonum lapathifolium* L.), green smartweed (*Polygonum scabrum* MOENCH), Oriental lady's thumb (*Persicaria longiseta*) or Nepalese Smartweed (*Persicaria nepalensis* (Meisn.) H. Gross); cucurbitaceae such as flexuous bittercress (*Cardamine flexuosa* WITH.); cucurbitaceae such as burcucumber (*Sicyos angulatus* L.); commelinaceae such as common dayflower (*Commelina communis* L.); rosaceae such as mock strawberry (*Duchesnea chrysantha* (Zoll. et Mor.) Miq.); molluginacea such as carpetweed (*Mollugo verticillata* L.); or rubiaceae such as false cleavers (*Galium spurium* var. *echinospermon* (Wallr.) Hayek) or stickywilly (*Galium aparine* L).

The herbicidal composition of the present invention is very useful for practical applications. For example, the following cases may be mentioned.

(1) The herbicidal composition of the present invention exhibits a remarkable synergistic effect and exhibits a good herbicidal effect even if the doses of both the compound A and the compound B are small, whereby an impact on the surrounding environment can be suppressed.

(2) There may be a case where it is possible to provide a herbicidal composition having a long lasting herbicidal effect i.e. a long lasting residual activity, as compared with a case where the compound A and the compound B are individually applied, respectively alone.

(3) There may be a case where it is possible to provide a herbicidal composition having a broad spectrum having high effects against both gramineae and broad leaf weeds, as compared with a case where the compound A and the compound B are individually applied, respectively alone.

(4) Since the compound A and the compound B are a combination of different modes of action, there may be a case where it is possible to prevent emergence of weeds resistant to herbicides or weeds having low sensitivity to herbicides.

(5) There may be a case where safety to crop plants can be improved as compared with a case where the compound A and the compound B are individually applied, respectively alone.

The herbicidal composition of the present invention may be used as mixed with the following known herbicidal compounds (common names, etc.), whereby the application range against weeds, the season for herbicidal treatment, the herbicidal activities, etc. may sometimes be improved to better directions. In a case where these compounds have their salts, alkyl esters, hydrates, different crystal forms, various structural isomers, etc., all of them are included, of course, even if no specific disclosure thereof is made.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium, aminopyralid, aminocyclopyrachlor or halauxifen; and others such as naptalam, naptalam-sodium, benazolin, benazolin-ethyl, quinclorac, quinmerac, diflufenzopyr, diflufenzopyr-sodium, fluroxypyr, fluroxypyr-2-butoxy-1-methylethyl, fluroxypyr-meptyl, chlorflurenol or chlorflurenol-methyl.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton or trietazine; a triazine type such as simazine, atrazine, atratone, simetryn, prometryn, dimethametryn, hexazinone, metribuzin, terbuthylazine, cyanazine, ametryn, cybutryne, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, amicarbazone, methazole, pentanochlor, or phenmedipham.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl fluoroglycofen-ethyl or fluoroglycofen; a cyclic imide type such as chlorphthalim, flumioxazin, flumiclorac, flumiclorac-pentyl, cinidon-ethyl or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, fluazolate, profluazol, flufenpyr-ethyl, bencarbazone, thiafenacil or pyrachlonil.

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone or pyrasulfotole; and others such as amitrole, fluridone, flurtamone, diflufenican, methoxyphenone, clomazone, sulcotrione, mesotrione, tembotrione, tefuryltrione, KUH-110, SW-065, isoxaflutole, difenzoquat, difenzoquat-metilsulfate, isoxachlortole, benzobicyclon, bicyclopyrone, picolinafen or beflubutamid.

(6) Those which are believed to exhibit herbicidal effects by inhibiting a fatty acid biosynthesis, such as an aryloxyphenoxypropionic add type such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; and a phenyl pyrazoline type such as pinoxaden.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, flazasulfuron, rimsulfuron, nicosulfuron, imazosulfuron, flucetosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, amidosulfuron, azimsulfuron, propyrisulfuron, metazosulfuron, methiopyrsulfuron, monosulfuron-mrthyl, or orsosulfuron; a triazolopyrimidinesulfonamide type such as flumetsulam, metosulam, diclosulam, cloransulam-methyl, florasulam, penoxsulam or pyroxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid or pyrimisulfan; a sulfonylaminocarbonyltriazolinone type such as flucarbazone, flucarbazone-sodium, propoxycarbazone-sodium, propoxycarbazone or thiencarbazone-methyl; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium or cinmethylin.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal, diphenamid, flamprop-M-methyl, flamprop-M or flamprop-M-isopropyl.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor, dimethenamid, dimethenamid-P, propisochlor or dimethachlor; a thiocarbamate type such as molinate, dimepiperate, pyributicarb, EPTC, butylate, vernolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone, fenoxasulfone, methiozolon, dalapon, dalapon-sodium, TCA-sodium or trichloroacetic acid.

(10) Those which are believed to exhibit herbicidal effects by inhibiting a cellulose biosynthesis of plants, such as dichlobenil, triaziflam, indaziflam or flupoxam.

(11) MSMA, DSMA, CMA, endothall, endothall-dipotassium, endothall-sodium, endothall-mono(N,N-dimethylalkylammonium), ethofumesate, sodium chlorate, pelargonic acid (nonanoic acid), fosamine, fosamine-ammonium, ipfencarbazone, aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, etc.

(12) Those which are believed to exhibit herbicidal effects by being parasitic on plants, such as *Xanthomonas campestris, Epicoccosirus nematosorus, Epicoccosirus nematosperus, Exserohilum monoseras* or *Drechsrela monoceras.*

The herbicidal composition of the present invention may be prepared by mixing the compounds A and B, as active ingredients, with various agricultural additives in accordance with conventional formulation methods for agricultural chemicals, and applied in various formulations such as dusts, granules, water dispersible granules (WG), wettable powders (WP), tablets, pills, capsules (including a formulation packaged by a water soluble film), water-based suspensions (SC), oil-based suspensions, microemulsions, suspoemulsions, water soluble powders, emulsifiable concentrates (EC), soluble concentrates or pastes. It may be formed into any formulation which is commonly used in this field, so long as the object of the present invention is thereby met.

At the time of the formulation, the compounds A and B may be mixed together for the formulation, or they may be separately formulated so that they may be mixed for use at the time of application.

The additives to be used for the formulation include, for example, a solid carrier such as kaolinite, sericite, diatomaceous earth, slaked lime, calcium carbonate, talc, white carbon, kaoline, bentonite, clay, sodium carbonate, sodium bicarbonate, mirabilite, zeolite or starch; a solvent such as water, toluene, xylene, solvent naphtha, dioxane, dimethylsulfoxide, N,N-dimethylformamide, dimethylacetamide, N-methyl-2-pyrrolidone or an alcohol; an anionic surfactant such as a salt of fatty acid, a benzoate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl ether phosphoric acid ester, a salt of polyoxyethylene aryl ether phosphoric acid ester, a naphthalene sulfonic acid condensed with formaldehyde or a salt of alkylnaphthalene sulfonic acid condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the active ingredient to such various additives in the herbicidal composition of the present invention may be from 0.001:99.999 to 95:5, preferably from 0.005:99.995 to 90:10.

As a method of applying the herbicidal composition of the present invention, a proper method can be employed among various methods depending upon various conditions such as the application site, the type of the formulation, and the type and the growth stage of the undesired plants to be controlled, and for example, the following methods may be mentioned.
1. The compound A and the compound B are formulated together, and the formulation is applied as it is.
2. The compound A and the compound B are formulated together, the formulation is diluted to a predetermined concentration with e.g. water, and as the case requires, a spreader (such as a surfactant, a vegetable oil or a mineral oil) is added for application.
3. The compound A and the compound B are separately formulated and applied as they are.
4, The compound A and the compound B are separately formulated, and they are diluted to a predetermined concentration with e,g, water, and as the case requires, a spreader (such as a surfactant, a vegetable oil or a mineral oil) is added for application.
5. The compound A and the compound B are separately formulated, and the formulations are mixed when diluted to a predetermined concentration with e.g. water, and as the case requires, a spreader (such as a surfactant, a vegetable oil or a mineral oil) is added for application.

Now, preferred embodiments of the present invention will be described below, but the present invention is by no means restricted thereto.

(1) A herbicidal composition comprising (A) metobromuron or its salt, and (B) at least one herbicidal compound selected from the group consisting of chlorpropham, S-metolachlor, flufenacet, pyroxasulfone, nicosulfuron, fluazifop-P-butyl, prometryn, ioxynil, pendimethalin, trifluralin, prosulfocarb, thiobencarb and indanofan, or its salt.

(2) The herbicidal composition according to the above (1), wherein the mixing ratio of (A) to (B) is from 200:1 to 1:40 by weight ratio.

(3) The herbicidal composition according to the above (1) or (2), wherein the herbicidal compound of (B) is chlorpropham, S-metolachlor, flufenacet, pyroxasulfone, nicosulfuron, fluazifop-P-butyl, prometryn, ioxynil, pendimethalin or trifluralin.

(4) The herbicidal composition according to the above (1) or (2), wherein the herbicidal compound of (B) is chlorpropham, S-metolachlor, flufenacet or pyroxasulfone.

(5) The herbicidal composition according to the above (1) or (2), wherein the herbicidal compound of (B) is chlorpropham, S-metolachlor, nicosulfuron, fluazifop-P-butyl, pendimethalin or trifluralin.

(6) A method for controlling undesired plants or inhibiting their growth, which comprises applying a herbicidally effective amount of (A) metobromuron or its salt, and a herbicidally effective amount of (B) at least one herbicidal compound selected from the group consisting of chlorpropham, S-metolachlor, flufenacet, pyroxasulfone, nicosulfuron, fluazifop-P-butyl, prometryn, ioxynil, pendimethalin, trifluralin, prosulfocarb, thiobencarb and indanofan, or its salt, to the undesired plants or to a place where they grow.

(7) The method according to the above (6), wherein (A) is applied in an amount of from 100 to 4,000 g/ha, and (B) is applied in an amount of from 20 to 4,000 g/ha.

(8) The method according to the above (6) or (7), wherein the herbicidal compound of (B) is chlorpropham, S-metolachlor, flufenacet, pyroxasulfone, nicosulfuron, fluazifop-P-butyl, prometryn, ioxynil, pendimethalin or trifluralin.

(9) The method according to the above (6) or (7), wherein the herbicidal compound of (B) is chlorpropham, S-metolachlor, flufenacet or pyroxasulfone.

(10) The method according to the above (6) or (7), wherein the herbicidal compound of (B) is chlorpropham, S-metolachlor, nicosulfuron, fluazifop-P-butyl, pendimethalin or trifluralin,

(11) The herbicidal composition according to the above (1), wherein (A) is metobromuron or its salt, and (B) is at least one herbicidal compound selected from the group consisting of chlorpropham, S-metolachlor, flufenacet, pyroxasulfone, nicosulfuron, fluazifop-P-butyl, prometryn, pendimethalin, trifluralin, prosulfocarb, thiobencarb and indanofan, or its salt.

(12) The herbicidal composition according to the above (11), wherein the mixing ratio of (A) to (B) is from 50:1 to 1:6 by weight ratio.

(13) The method according to the above (6), wherein (A) is metobromuron or its salt, and (B) is at least one herbicidal compound selected from the group consisting of chlorpropham, S-metolachlor, flufenacet, pyroxasulfone, nicosulfuron, fluazifop-P-butyl, prometryn, pendimethalin, trifluralin, prosulfocarb, thiobencarb and indanofan, or its salt, to the undesired plants or to a place where they grow.

(14) The method according to the above (13), wherein (A) and (B) are applied as mixed in a weight ratio of from 50:1 to 1:6.

EXAMPLES

Now, the present invention will be described in more detail with reference to Examples, but it should be understood that the present invention is by no means restricted thereto.

Test Example 1

In a soybean agricultural field (1.8 square meters per one test section) having seeds of barnyardgrass (*Echinochloa* crus-qalli L.) sown, predetermined amounts of SC containing metobromuron as active ingredient (trade name: Metobromuron 500 SC, manufactured by Belchim Crop Protection) and EC containing chlorpropham as active ingredient (trade name: KURORO IPC "ISHIHARA", manufactured by Ishihara Sangyo Kaisha, Ltd.) were diluted with water corresponding to 1,000 L per hectare and applied for soil treatment, prior to germination of soybean and weeds.

On the 19th day after treatment, the state of growth of barnyardgrass was visually observed and evaluated in accordance with the following standards. The growth inhibition rate (%) [measured value] and the growth inhibition rate (%) [calculated value] calculated by the Colby's method, are shown in Table 2.

Growth inhibition rate (%)=inhibition rate) (%) of 0 (equivalent to the non-treated area) to 100 (complete kill)

TABLE 2

| Compound | Dose (g/ha) | Growth inhibition rate of barnyardgrass (%) | |
|---|---|---|---|
| | | Measured value | Calculated value |
| Metobromuron | 1000 | 58 | — |
| Chlorpropham | 916 | 8 | — |
| Metobromuron + Chlorpropham | 1000 + 916 | 72 | 61 |

Test Example 2

In a soybean agricultural field (1.8 square meters per one test section) having seeds of spotted knotweed (Polygonum lapathifolium L.) sown, predetermined amounts of SC containing metobromuron as active ingredient (same as in Test Example 1) and EC containing S-metolachlor as active ingredient (trade name: DualGold, manufactured by Syngenta) were diluted with water corresponding to 1,000 L per hectare and applied for soil treatment, prior to germination of soybean and weeds.

On the 50th day after treatment, the state of growth of spotted knotweed was visually observed and evaluated in the same manner as in Test Example 1. The results are shown in Table 3.

TABLE 3

| Compound | Dose (g/ha) | Growth inhibition rate of spotted knotweed (%) | |
|---|---|---|---|
| | | Measured value | Calculated value |
| Metobromuron | 1000 | 58 | — |
| S-Metolachlor | 1000 | 59 | — |
| Metobromuron + S-Metolachlor | 1000 + 1000 | 89 | 83 |

Test Example 3

In a soybean agricultural field (8.4 square meters per one test section), predetermined amounts of SC containing metobromuron as active ingredient (same as in Test Example 1) and EC containing S-metolachlor as active ingredient (same as in Test Example 2) were diluted with water corresponding to 1,000 L per hectare and applied for soil treatment, prior to germination of soybean and weeds, On the 50th day after treatment, the state of growth of Nepalese Smartweed (Persicaria nepalensis (Meisn.) H. Gross) which occurred naturally, was visually observed and evaluated in the same manner as in Test Example 1. The results are shown in Table 4.

TABLE 4

| Compound | Dose (g/ha) | Growth inhibition rate of Nepalese Smartweed (%) | |
|---|---|---|---|
| | | Measured value | Calculated value |
| Metobromuron | 1500 | 30 | — |
| S-Metolachlor | 1000 | 10 | — |
| Metobromuron + S-Metolachlor | 1500 + 1000 | 60 | 37 |

Test Example 4

In a soybean agricultural field (8.4 square meters per one test section), predetermined amounts of SC containing metobromuron as active ingredient (same as in Test Example 1) and EC containing trifluralin as active ingredient (trade name: TOREFANOCIDE NYUZAI, manufactured by Dow AgroScience) were diluted with water corresponding to 1,000 L per hectare and applied for soil treatment, prior to germination of soybean and weeds.

On the 50th day after treatment, the state of growth of barnyardgrass (Echinochloa crus-qalli L.) which occurred naturally, was visually observed and evaluated in the same manner as in Test Example 1. The results are shown in Table 5.

TABLE 5

| Compound | Dose (g/ha) | Growth inhibition rate of barnyardgrass (%) | |
|---|---|---|---|
| | | Measured value | Calculated value |
| Metobromuron | 1000 | 30 | — |
| Trifluralin | 890 | 20 | — |
| Metobromuron + Trifluralin | 1000 + 890 | 59 | 44 |

Test Example 5

In an adzuki bean agricultural field (9.6 square meters per one test section), predetermined amounts of SC containing metobromuron as active ingredient (same as in Test Example 1) and EC containing fluazifop-P-butyl as active ingredient (trade name: ONECIDE P NYUZAI, manufactured by Ishihara Sangyo Kaisha, Ltd.) were diluted with water corresponding to 1,000 L per hectare and applied for soil treatment, prior to germination of adzuki bean and weeds.

On the 39th day after treatment, the state of growth of barnyardgrass (Echinochloa crus-qalli L.) which occurred naturally, was visually observed and evaluated in the same manner as in Test Example 1. The results are shown in Table 6.

TABLE 6

| Compound | Dose (g/ha) | Growth inhibition rate of barnyardgrass (%) | |
|---|---|---|---|
| | | Measured value | Calculated value |
| Metobromuron | 1000 | 53 | — |
| Fluazifop-P-butyl | 700 | 55 | — |

TABLE 6-continued

| Compound | Dose (g/ha) | Growth inhibition rate of barnyardgrass (%) | |
|---|---|---|---|
| | | Measured value | Calculated value |
| Metobromuron + Fluazifop-P-butyl | 1000 + 700 | 85 | 79 |

Test Example 6

In an adzuki bean agricultural field (9.6 square meters per one test section), predetermined amounts of SC containing metobromuron as active ingredient (same as in Test Example 1) and EC containing S-metolachlor as active ingredient (same as in Test Example 2) were diluted with water corresponding to 1,000 L per hectare and applied for soil treatment, prior to germination of adzuki bean and weeds.

On the 39th day after treatment, the state of growth of Nepalese Smartweed (*Persicaria nepalensis* (Meisn.) H. Gross) which occurred naturally, was visually observed and evaluated in the same manner as in Test Example 1. The results are shown in Table 7.

TABLE 7

| Compound | Dose (g/ha) | Growth inhibition rate of Nepalese Smartweed (%) | |
|---|---|---|---|
| | | Measured value | Calculated value |
| Metobromuron | 1000 | 35 | — |
| | 1500 | 40 | — |
| S-Metolachlor | 1000 | 75 | — |
| Metobromuron + S-Metolachlor | 1000 + 1000 | 100 | 84 |
| | 1500 + 1000 | 93 | 85 |

Test Example 7

In a common bean (*Phaseolus vulgaris*) agricultural field (4.8 square meters per one test section), predetermined amounts of SC containing metobromuron as active ingredient (same as in Test Example 1) and EC containing trifluralin as active ingredient (same as in Test Example 4) were diluted with water corresponding to 1,000 L per hectare and applied for soil treatment, prior to germination of common bean and weeds.

On the 49th day after treatment, the state of growth of Oriental lady's thumb (*Persicaria longiseta*) which occurred naturally, was visually observed and evaluated in the same manner as in Test Example 1. The results are shown in Table 8.

TABLE 8

| Compound | Dose (g/ha) | Growth inhibition rate of Oriental lady's thumb (%) | |
|---|---|---|---|
| | | Measured value | Calculated value |
| Metobromuron | 1500 | 10 | — |
| Trifluralin | 1335 | 40 | — |
| Metobromuron + Trifluralin | 1500 + 1335 | 54 | 46 |

Test Example 8

In a corn agricultural field (9.6 square meters per one test section), predetermined amounts of SC containing metobromuron as active ingredient (same as in Test Example 1) and EC containing S-metolachlor as active ingredient (same as in Test Example 2) were diluted with water corresponding to 1,000 L per hectare and applied for soil treatment, prior to germination of corn and weeds.

On the 28th day after treatment, the state of growth of common lambsquarters (*Chenopodium album* L.) which occurred naturally, was visually observed and evaluated in the same manner as in Test Example 1. The results are shown in Table 9.

TABLE 9

| Compound | Dose (g/ha) | Growth inhibition rate of common lambsquarters (%) | |
|---|---|---|---|
| | | Measured value | Calculated value |
| Metobromuron | 1000 | 78 | — |
| S-Metolachlor | 1000 | 69 | — |
| Metobromuron + S-Metolachlor | 1000 + 1000 | 100 | 93 |

Test Example 9

In a corn agricultural field (9.6 square meters per one test section), predetermined amounts of SC containing metobromuron as active ingredient (same as in Test Example 1) and EC containing S-metolachlor as active ingredient (same as in Test Example 2) were diluted with water corresponding to 1,000 L per hectare and applied for soil treatment, prior to germination of corn and weeds.

On the 49th day after treatment, the state of growth of redroot pigweed (*Amaranthus retroflexus* L.) which occurred naturally, was visually observed and evaluated in the same manner as in Test Example 1. The results are shown in Table 10.

TABLE 10

| Compound | Dose (g/ha) | Growth inhibition rate of redroot pigweed (%) | |
|---|---|---|---|
| | | Measured value | Calculated value |
| Metobromuron | 1000 | 25 | — |
| S-Metolachlor | 1000 | 45 | — |
| Metobromuron + S-Metolachlor | 1000 + 1000 | 77 | 59 |

Test Example 10

In a corn agricultural field (9.6 square meters per one test section), predetermined amounts of SC containing metobromuron as active ingredient (same as in Test Example 1) and EC containing pendimethalin as active ingredient (trade name: GOGO SAN NYUZAI, manufactured by BASF) were diluted with water corresponding to 1,000 L per hectare and applied for soil treatment, prior to germination of corn and weeds.

On the 49th day after treatment, the state of growth of polygonaceae weeds which occurred naturally, was visually observed and evaluated in the same manner as in Test Example 1. The results are shown in Table 11.

TABLE 11

| Compound | Dose (g/ha) | Growth inhibition rate of Polygonaceae weeds (%) | |
| --- | --- | --- | --- |
| | | Measured value | Calculated value |
| Metobromuron | 1000 | 30 | — |
| Pendimethalin | 600 | 73 | — |
| Metobromuron + Pendimethalin | 1000 + 600 | 100 | 81 |

Test Example 11

In a corn agricultural field (3.6 square meters per one test section) having seeds of large crabgrass (*Diqitaria sanquinalis* L.) sown, when large crabgrass reached from 1.5 to 2.0 leaf stage, predetermined amounts of SC containing metobromuron as active ingredient (same as in Test Example 1) and SC containing nicosulfuron as active ingredient were diluted with water (corresponding to 300 L per hectare) containing 0.67 vol % of an agricultural spreader (trade name: Actirob B, manufactured by Bayer CropScience) and applied for foliar treatment.

On the 30th day after treatment, the state of growth of large crabgrass was visually observed and evaluated in the same manner as in Test Example 1. The results are shown in Table 12.

TABLE 12

| Compound | Dose (g/ha) | Growth inhibition rate of large crabgrass (%) | |
| --- | --- | --- | --- |
| | | Measured value | Calculated value |
| Metobromuron | 1000 | 25 | — |
| Nicosulfuron | 30 | 10 | — |
| Metobromuron + Nicosulfuron | 1000 + 30 | 58 | 33 |

Test Example 12

In a corn agricultural field (3.6 square meters per one test section), predetermined amounts of SC containing metobromuron as active ingredient (same as in Test Example 1) and SC containing nicosulfuron as active ingredient were diluted with water (corresponding to 300 L per hectare) containing 0.67 vol % of an agricultural spreader (same as in Test Example 11) and applied for soil treatment, prior to germination of weeds.

On the 30th day after treatment, the state of growth of common purslane (*Portulaca oleracea* L.) which occurred naturally, was visually observed and evaluated in the same manner as in Test Example 1. The results are shown in Table 13.

TABLE 13

| Compound | Dose (g/ha) | Growth inhibition rate of common purslane (%) | |
| --- | --- | --- | --- |
| | | Measured value | Calculated value |
| Metobromuron | 1000 | 85 | — |
| Nicosulfuron | 30 | 55 | — |
| Metobromuron + Nicosulfuron | 1000 + 30 | 100 | 93 |

Test Example 13

Soil was put into a 1/300,000 ha pot, and seeds of velvetleaf (*Abutilon theophrasti* MEDIC.) were sown. Prior to germination of velvetleaf, predetermined amounts of SC containing metobromuron as active ingredient (same as in Test Example 1) and WG containing pyroxasulfone as active ingredient (trade name: Sakura 850 WG, manufactured by Bayer CropScience) were diluted with water corresponding to 1,000 L per hectare and applied for soil treatment.

On the 12th day after treatment, the state of growth of velvetleaf was visually observed and evaluated in the same manner as in Test Example 1. The results are shown in Table 14.

TABLE 14

| Compound | Dose (g/ha) | Growth inhibition rate of velvetleaf (%) | |
| --- | --- | --- | --- |
| | | Measured value | Calculated value |
| Metobromuron | 375 | 28 | — |
| | 750 | 55 | — |
| | 1500 | 74 | — |
| Pyroxasulfone | 25 | 25 | — |
| | 33 | 28 | — |
| | 50 | 38 | — |
| Metobromuron + Pyroxasulfone | 375 + 25 | 60 | 46 |
| | 375 + 33 | 63 | 48 |
| | 375 + 50 | 82 | 55 |
| | 750 + 25 | 79 | 66 |
| | 750 + 33 | 83 | 68 |
| | 750 + 50 | 91 | 72 |
| | 1500 + 25 | 100 | 81 |
| | 1500 + 33 | 100 | 81 |
| | 1500 + 50 | 100 | 84 |

Test Example 14

Soil was put into a 1/300,000 ha pot, and seeds of black nightshade (*Solanum nigrum* L.) were sown. Prior to germination of black nightshade, predetermined amounts of SC containing metobromuron as active ingredient (same as in Test Example 1) and WG containing pyroxasulfone as active ingredient (same as in Test Example 13) were diluted with water corresponding to 1,000 L per hectare and applied for soil treatment.

On the 12th day after treatment, the state of growth of black nightshade was visually observed and evaluated in the same manner as in Test Example 1. The results are shown in Table 15.

TABLE 15

| Compound | Dose (g/ha) | Growth inhibition rate of black nightshade (%) | |
| --- | --- | --- | --- |
| | | Measured value | Calculated value |
| Metobromuron | 375 | 64 | — |
| | 750 | 83 | — |
| Pyroxasulfone | 25 | 50 | — |
| | 33 | 64 | — |
| | 50 | 73 | — |
| Metobromuron + Pyroxasulfone | 375 + 25 | 99 | 82 |
| | 375 + 33 | 99 | 87 |
| | 375 + 50 | 99 | 90 |
| | 750 + 25 | 100 | 92 |
| | 750 + 33 | 100 | 94 |

Test Example 15

Soil was put into a 1/300,000 ha pot, and seeds of barnyardgrass (*Echinochloa crus-galli* L.) were sown. On the day after seeding, predetermined amounts of SC containing metobromuron as active ingredient (same as in Test Example 1) and EC containing chlorpropham as active ingredient (same as in Test Example 1) were diluted with water corresponding to 1,000 L per hectare and applied for soil treatment.

On the 21st day after treatment, the state of growth of barnyardgrass was visually observed and evaluated in the same manner as in Test Example 1. The results are shown in Table 16.

TABLE 16

| Compound | Dose (g/ha) | Growth inhibition rate of barnyardgrass (%) | |
|---|---|---|---|
| | | Measured value | Calculated value |
| Metobromuron | 1500 | 72 | — |
| Chlorpropham | 750 | 0 | — |
| Metobromuron + Chlorpropham | 1500 + 750 | 83 | 72 |

Test Example 16

The test was carried out in the same manner as in Test Example 15 except that barnyardgrass (*Echinochloa crus-galli* L.) was changed to giant foxtail (*Setaria faberi* Herrm.), to obtain the results as shown in Table 17. However, the doses of the active ingredients were as shown in Table 17.

TABLE 17

| Compound | Dose (g/ha) | Growth inhibition rate of giant foxtail (%) | |
|---|---|---|---|
| | | Measured value | Calculated value |
| Metobromuron | 1000 | 78 | — |
| Chlorpropham | 750 | 0 | — |
| | 1000 | 0 | — |
| Metobromuron + Chlorpropham | 1000 + 750 | 98 | 78 |
| | 1000 + 1000 | 97 | 78 |

Test Example 17

The test was carried out in the same manner as in Test Example 15 except that barnyardgrass (*Echinochloa crus-galli* L.) was changed to black nightshade (*Solanum nigrum* L.), to obtain the results as shown in Table 18. However, the doses of the active ingredients were as shown in Table 18.

TABLE 18

| Compound | Dose (g/ha) | Growth inhibition rate of black nightshade (%) | |
|---|---|---|---|
| | | Measured value | Calculated value |
| Metobromuron | 1000 | 78 | — |
| Chlorpropham | 750 | 0 | — |
| | 1000 | 0 | — |
| Metobromuron + Chlorpropham | 1000 + 750 | 98 | 78 |
| | 1000 + 1000 | 97 | 78 |

Test Example 18

Soil was put into a 1/300,000 ha pot, and seeds of barnyardgrass (*Echinochloa crus-galli* L.) were sown. On the day after seeding, predetermined amounts of SC containing metobromuron as active ingredient (same as in Test Example 1) and EC containing chlorpropham as active ingredient (same as in Test Example 1) were diluted with water corresponding to 1,000 L per hectare and applied for soil treatment.

On the 26th day after treatment, the state of growth of barnyardgrass was visually observed and evaluated in the same manner as in Test Example 1. The results are shown in Table 19.

TABLE 19

| Compound | Dose (g/ha) | Growth inhibition rate of barnyardgrass (%) | |
|---|---|---|---|
| | | Measured value | Calculated value |
| Metobromuron | 188 | 0 | — |
| Chlorpropham | 500 | 70 | — |
| Metobromuron + Chlorpropham | 188 + 500 | 92 | 70 |

Test Example 19

The test was carried out in the same manner as in Test Example 18 except that barnyardgrass (*Echinochloa crus-galli* L.) was changed to annual bluegrass (*Poa annua* L.), to obtain the results as shown in Table 20. However, the doses of the active ingredients were as shown in Table 20.

TABLE 20

| Compound | Dose (g/ha) | Growth inhibition rate of annual bluegrass (%) | |
|---|---|---|---|
| | | Measured value | Calculated value |
| Metobromuron | 375 | 50 | — |
| Chlorpropham | 250 | 10 | — |
| Metobromuron + Chlorpropham | 375 + 250 | 75 | 55 |

Test Example 20

The test was carried out in the same manner as in Test Example 18 except that barnyardgrass (*Echinochloa crus-galli* L.) was changed to common lambsquarters (*Chenopodium album* L.), to obtain the results as shown in Table 21. However, the doses of the active ingredients were as shown in Table 21.

TABLE 21

| Compound | Dose (g/ha) | Growth inhibition rate of common lambsquarters (%) | |
|---|---|---|---|
| | | Measured value | Calculated value |
| Metobromuron | 188 | 50 | — |
| Chlorpropham | 125 | 20 | — |
| | 250 | 30 | — |
| | 1000 | 50 | — |
| Metobromuron + Chlorpropham | 188 + 125 | 89 | 60 |
| | 188 + 250 | 92 | 65 |
| | 188 + 1000 | 95 | 75 |

Test Example 21

Soil was put into a 1/300,000 ha pot, and seeds of barnyardgrass (*Echinochloa crus-qalli* L.) were sown. On the day after seeding, predetermined amounts of SC containing metobromuron as active ingredient (same as in Test Example 1) and WP containing prometryn as active ingredient (trade name: Gesagard 50, manufactured by Nippon Kayaku Co., Ltd.) were diluted with water corresponding to 1,000 L per hectare and applied for soil treatment.

On the 21st day after treatment, the state of growth of barnyardgrass was visually observed and evaluated in the same manner as in Test Example 1. The results are shown in Table 22.

TABLE 22

| Compound | Dose (g/ha) | Growth inhibition rate of barnyardgrass (%) Measured value | Calculated value |
|---|---|---|---|
| Metobromuron | 750 | 20 | — |
|  | 1000 | 43 | — |
|  | 1500 | 72 | — |
| Prometryn | 300 | 15 | — |
|  | 400 | 38 | — |
| Metobromuron + Prometryn | 750 + 300 | 87 | 32 |
|  | 750 + 400 | 83 | 50 |
|  | 1000 + 300 | 98 | 52 |
|  | 1000 + 400 | 97 | 65 |
|  | 1500 + 300 | 98 | 76 |
|  | 1500 + 400 | 97 | 83 |

Test Example 22

The test was carried out in the same manner as in Test Example 21 except that barnyardgrass (*Echinochloa crus-qalli* L.) was changed to large crabgrass (*Diqitaria sanquinalis* L.), to obtain the results as shown in Table 23. However, the doses of the active ingredients were as shown in Table 23.

TABLE 23

| Compound | Dose (g/ha) | Growth inhibition rate of large crabgrass (%) Measured value | Calculated value |
|---|---|---|---|
| Metobromuron | 750 | 33 | — |
|  | 1000 | 50 | — |
| Prometryn | 300 | 62 | — |
|  | 400 | 76 | — |
| Metobromuron + Prometryn | 750 + 300 | 98 | 75 |
|  | 750 + 400 | 98 | 84 |
|  | 1000 + 300 | 100 | 81 |
|  | 1000 + 400 | 100 | 88 |

Test Example 23

Soil was put into a 1/300,000 ha pot, and seeds of black nightshade (*Solanum nigrum* L.) were sown. On the day after seeding, predetermined amounts of SC containing metobromuron as active ingredient (same as in Test Example 1) and EC containing fluazifop-P-butyl as active ingredient (same as in Test Example 5) were diluted with water corresponding to 1,000 L per hectare and applied for soil treatment.

On the 20th day after treatment, the state of growth of black nightshade was visually observed and evaluated in the same manner as in Test Example 1. The results are shown in Table 24.

TABLE 24

| Compound | Dose (g/ha) | Growth inhibition rate of black nightshade (%) Measured value | Calculated value |
|---|---|---|---|
| Metobromuron | 750 | 85 | — |
| Fluazifop-P-butyl | 131.25 | 25 | — |
| Metobromuron + Fluazifop-P-butyl | 750 + 131.25 | 98 | 89 |

Test Example 24

Soil was put into a 1/300,000 ha pot, and seeds of common lambsquarters (*Chenopodium album* L.) were sown. On the day after seeding, predetermined amounts of SC containing metobromuron as active ingredient (same as in Test Example 1) and EC containing trifluralin as active ingredient (same as in Test Example 4) were diluted with water corresponding to 1,000 L per hectare and applied for soil treatment.

On the 21st day after treatment, the state of growth of common lambsquarters was visually observed and evaluated in the same manner as in Test Example 1. The results are shown in Table 25.

TABLE 25

| Compound | Dose (g/ha) | Growth inhibition rate of common lambsquarters (%) Measured value | Calculated value |
|---|---|---|---|
| Metobromuron | 375 | 50 | — |
| Trifluralin | 296.7 | 20 | — |
|  | 445 | 15 | — |
|  | 667.5 | 48 | — |
| Metobromuron + Trifluralin | 375 + 296.7 | 93 | 60 |
|  | 375 + 445 | 88 | 58 |
|  | 375 + 667.5 | 88 | 74 |

Test Example 25

The test was carried out in the same manner as in Test Example 24 except that common lambsquarters (*Chenopodium album* L.) was changed to common chickweed (*Stellaria media* L.), to obtain the results as shown in Table 26. However, the doses of the active ingredients were as shown in Table 26.

TABLE 26

| Compound | Dose (g/ha) | Growth inhibition rate of common chickweed (%) Measured value | Calculated value |
|---|---|---|---|
| Metobromuron | 250 | 73 | — |
| Trifluralin | 445 | 35 | — |
| Metobromuron + Trifluralin | 250 + 445 | 90 | 82 |

Test Example 26

Soil was put into a 1/300,000 ha pot, and seeds of black nightshade (*Solanum nigrum* L.) were sown. On the day after seeding, predetermined amounts of SC containing metobromuron as active ingredient (same as in Test Example 1) and EC containing prosulfocarb as active ingredient (trade name: BOXER NYUZAI, manufactured by Syngenta) were diluted with water corresponding to 1,000 L per hectare and applied for soil treatment.

On the 21st day after treatment, the state of growth of black nightshade was visually observed and evaluated in the same manner as in Test Example 1. The results are shown in Table 27.

TABLE 27

| Compound | Dose (g/ha) | Growth inhibition rate of black nightshade (%) | |
|---|---|---|---|
| | | Measured value | Calculated value |
| Metobromuron | 250 | 25 | — |
| | 375 | 50 | — |
| | 562.5 | 68 | — |
| Prosulfocarb | 653.4 | 50 | — |
| | 980 | 50 | — |
| | 1470 | 50 | — |
| Metobromuron + Prosulfocarb | 250 + 653.4 | 91 | 63 |
| | 250 + 980 | 84 | 63 |
| | 250 + 1470 | 93 | 63 |
| | 375 + 653.4 | 99 | 75 |
| | 375 + 980 | 100 | 75 |
| | 375 + 1470 | 100 | 75 |
| | 562.5 + 653.4 | 100 | 84 |
| | 562.5 + 980 | 100 | 84 |
| | 562.5 + 1470 | 100 | 84 |

Test Example 27

The test was carried out in the same manner as in Test Example 26 except that EC containing prosulfocarb as active ingredient was changed to SC containing flufenacet as active ingredient (trade name: Cadou, manufactured by Bayer CropScience), to obtain the results as shown in Table 28. However, the doses of the active ingredients were as shown in Table 28.

TABLE 28

| Compound | Dose (g/ha) | Growth inhibition rate of black nightshade (%) | |
|---|---|---|---|
| | | Measured value | Calculated value |
| Metobromuron | 250 | 25 | — |
| | 375 | 50 | — |
| | 562.5 | 68 | — |
| Flufenacet | 83.35 | 30 | — |
| | 125 | 25 | — |
| | 187.5 | 40 | — |
| Metobromuron + Flufenacet | 250 + 83.35 | 55 | 48 |
| | 250 + 125 | 70 | 44 |
| | 250 + 187.5 | 83 | 55 |
| | 375 + 83.35 | 84 | 65 |
| | 375 + 125 | 85 | 63 |
| | 375 + 187.5 | 94 | 70 |
| | 562.5 + 83.35 | 90 | 78 |
| | 562.5 + 125 | 98 | 76 |
| | 562.5 + 187.5 | 95 | 81 |

Test Example 28

Soil was put into a 1/300,000 ha pot, and seeds of large crabgrass (*Digitaria sanquinalis* L.) were sown. On the day after seeding, predetermined amounts of SC containing metobromuron as active ingredient (same as in Test Example 1) and EC containing pendimethalin as active ingredient (same as in Test Example 10) were diluted with water corresponding to 1,000 L per hectare and applied for soil treatment.

On the 27th day after treatment, the state of growth of large crabgrass was visually observed and evaluated in the same manner as in Test Example 1. The results are shown in Table 29.

TABLE 29

| Compound | Dose (g/ha) | Growth inhibition rate of large crabgrass (%) | |
|---|---|---|---|
| | | Measured value | Calculated value |
| Metobromuron | 62.5 | 0 | — |
| | 125 | 15 | — |
| | 250 | 35 | — |
| Pendimethalin | 62.5 | 70 | — |
| Metobromuron + Pendimethalin | 62.5 + 62.5 | 98 | 70 |
| | 125 + 62.5 | 98 | 75 |
| | 250 + 62.5 | 98 | 81 |

Test Example 29

Soil was put into a 1/300,000 ha pot, and seeds of large crabgrass (*Digitaria sanquinalis* L.) were sown. On the day after seeding, predetermined amounts of SC containing metobromuron as active ingredient (same as in Test Example 1) and WP containing indanofan as active ingredient were diluted with water corresponding to 1,000 L per hectare and applied for soil treatment.

On the 20th day after treatment, the state of growth of large crabgrass was visually observed and evaluated in the same manner as in Test Example 1. The results are shown in Table 30.

TABLE 30

| Compound | Dose (g/ha) | Growth inhibition rate of large crabgrass (%) | |
|---|---|---|---|
| | | Measured value | Calculated value |
| Metobromuron | 250 | 30 | — |
| | 375 | 50 | — |
| | 562.5 | 80 | — |
| Indanofan | 25 | 25 | — |
| | 37.5 | 25 | — |
| | 56.3 | 28 | — |
| Metobromuron + Indanofan | 250 + 25 | 74 | 48 |
| | 250 + 37.5 | 99 | 48 |
| | 250 + 56.3 | 100 | 50 |
| | 375 + 25 | 94 | 63 |
| | 375 + 37.5 | 100 | 63 |
| | 375 + 56.3 | 100 | 64 |
| | 562.5 + 25 | 90 | 85 |
| | 562.5 + 37.5 | 95 | 85 |
| | 562.5 + 56.3 | 96 | 86 |

Test Example 30

Soil was put into a 1/300,000 ha pot, and seeds of common lambsquarters (*Chenopodium album* L.) were sown. On the day after seeding, predetermined amounts of SC containing metobromuron as active ingredient (same as in Test Example 1) and EC containing thiobencarb as active ingredient (trade name: Saturn NYUZAI, manufactured by KUMIAI CHEMICAL INDUSTRY Co., Ltd.) were diluted with water corresponding to 1,000 L per hectare and applied for soil treatment.

On the 20th day after treatment, the state of growth of common lambsquarters was visually observed and evaluated in the same manner as in Test Example 1. The results are shown in Table 31.

TABLE 31

| Compound | Dose (g/ha) | Growth inhibition rate of common lambsquarters (%) | |
|---|---|---|---|
| | | Measured value | Calculated value |
| Metobromuron | 250 | 78 | — |
| Thiobencarb | 296.3 | 0 | — |
| | 444.4 | 0 | — |
| | 666.7 | 0 | — |
| Metobromuron + | 250 + 296.3 | 89 | 78 |
| Thiobencarb | 250 + 444.4 | 98 | 78 |
| | 250 + 666.7 | 95 | 78 |

Test Example 31

The test was carried out in the same manner as in Test Example 30 except that common lambsquarters (*Chenopodium album* L.) was changed to black nightshade (*Solanum nigrum* L.), to obtain the results as shown in Table 32. However, the doses of the active ingredients were as shown in Table 32.

TABLE 32

| Compound | Dose (g/ha) | Growth inhibition rate of black nightshade (%) | |
|---|---|---|---|
| | | Measured value | Calculated value |
| Metobromuron | 375 | 65 | — |
| | 562.5 | 76 | — |
| Thiobencarb | 296.3 | 25 | — |
| | 444.4 | 23 | — |
| | 666.7 | 20 | — |
| Metobromuron + | 375 + 296.3 | 81 | 74 |
| Thiobencarb | 375 + 444.4 | 83 | 73 |
| | 375 + 666.7 | 84 | 72 |
| | 562.5 + 296.3 | 98 | 82 |
| | 562.5 + 444.4 | 99 | 82 |
| | 562.5 + 666.7 | 100 | 81 |

Test Example 32

The test was carried out in the same manner as in Test Example 18 to obtain the results as shown in Table 33. However, the doses of the active ingredients were as shown in Table 33.

TABLE 33

| Compound | Dose (g/ha) | Growth inhibition rate of barnyardgrass (%) | |
|---|---|---|---|
| | | Measured value | Calculated value |
| Metobromuron | 375 | 40 | — |
| Chlorpropham | 125 | 10 | — |
| | 250 | 0 | — |
| | 500 | 70 | — |

TABLE 33-continued

| Compound | Dose (g/ha) | Growth inhibition rate of barnyardgrass (%) | |
|---|---|---|---|
| | | Measured value | Calculated value |
| Metobromuron + | 375 + 125 | 60 | 46 |
| Chlorpropham | 375 + 250 | 85 | 40 |
| | 375 + 500 | 89 | 82 |

INDUSTRIAL APPLICABILITY

The herbicidal composition and method of the present invention may be applied to various fields including agricultural fields such as upland fields, orchards and paddy fields, and non-cropland such as ridges of fields, fallow fields, play grounds, golf courses, vacant lands, forests, factory sites, railway sides and roadsides.

The entire disclosure of Japanese Patent Application No. 2014-215428 filed on Oct. 22, 2014 including specification, claims and summary is incorporated herein by reference in its entirety.

The invention claimed is:

1. A herbicidal composition comprising a synergistically effective amount of (A) metobromuron or its salt, and (B) at least one herbicidal compound selected from the group consisting of chlorpropham, flufenacet, pyroxasulfone, nicosulfuron, prosulfocarb, thiobencarb and indanofan, or its alkyl ester or its salt.

2. The herbicidal composition according to claim 1, wherein the mixing ratio of (A) to (B) is from 200:1 to 1:40 by weight.

3. The herbicidal composition according to claim 1, wherein (A) is metobromuron or its salt, and (B) is at least one herbicidal compound selected from the group consisting of chlorpropham, pyroxasulfone, nicosulfuron, prosulfocarb, thiobencarb and indanofan, or its salt.

4. The herbicidal composition according to claim 3, wherein the mixing ratio of (A) to (B) is from 50:1 to 1:6 by weight.

5. The herbicidal composition according to claim 1, wherein (A) is metobromuron or its salt, and (B) is pyroxasulfone or its salt.

6. The herbicidal composition according to claim 5, wherein the mixing ratio of (A) to (B) is from 200:1 to 1:40 by weight.

7. The herbicidal composition according to claim 5, wherein the mixing ratio of (A) to (B) is from 50:1 to 1:6 by weight.

8. The herbicidal composition according to claim 5, wherein the mixing ratio of (A) to (B) is from 100:1 to 1:1 by weight.

9. The herbicidal composition according to claim 5, wherein the mixing ratio of (A) to (B) is from 50:1 to 7:1 by weight.

10. A method for controlling undesired plants or inhibiting their growth, which comprises applying a herbicidally effective amount of (A) metobromuron or its salt, and a herbicidally effective amount of (B) at least one herbicidal compound selected from the group consisting of chlorpropham, flufenacet, pyroxasulfone, nicosulfuron, prosulfocarb, thiobencarb and indanofan, or its alkyl ester or its salt, to the undesired plants or to a place where they grow; wherein the applying of (A) and (B) together exhibits synergy.

11. The method according to claim 10, wherein (A) is applied in an amount of from 100 to 4,000 g/ha, and (B) is applied in an amount of from 20 to 4,000 g/ha.

12. The method according to claim 10, wherein (A) and (B) are applied as mixed in a weight ratio of from 200:1 to 1:40.

13. The method according to claim 10, wherein (A) is metobromuron or its salt, and (B) is at least one herbicidal compound selected from the group consisting of chlorpropham, pyroxasulfone, nicosulfuron, prosulfocarb, thiobencarb and indanofan, or its salt.

14. The method according to claim 13, wherein (A) and (B) are applied as mixed in a weight ratio of from 50:1 to 1:6.

15. The method according to claim 10, wherein (A) is metobromuron or its salt, and (B) is pyroxasulfone or its salt.

16. The method according to claim 15, wherein (A) is applied in an amount of from 100 to 4,000 g/ha, and (B) is applied in an amount of from 20 to 4,000 g/ha.

17. The method according to claim 15, wherein (A) is applied in an amount of from 60 to 1,500 g/ha, and (B) is applied in an amount of from 25 to 1,500 g/ha.

18. The method according to claim 15, wherein (A) and (B) are applied as mixed in a weight ratio of from 200:1 to 1:40.

19. The method according to claim 15, wherein (A) and (B) are applied as mixed in a weight ratio of from 100:1 to 1:1.

20. The method according to claim 15, wherein (A) and (B) are applied as mixed in a weight ratio of from 50:1 to 7:1.

* * * * *